US00RE43115E

(19) United States
(12) Reissued Patent
Duran et al.

(10) Patent Number: US RE43,115 E
(45) Date of Reissued Patent: Jan. 17, 2012

(54) PROCESS FOR THE MANUFACTURE OF FUSED PIPERAZIN-2-ONE DERIVATIVES

(75) Inventors: Adil Duran, Biberach an der Riss (DE); Guenter Linz, Mittelbiberach (DE)

(73) Assignee: Boehringer Ingelheim International GmbH, Ingelheim am Rhein (DE)

(21) Appl. No.: 12/850,993

(22) Filed: Aug. 5, 2010

Related U.S. Patent Documents

Reissue of:
(64) Patent No.: 7,238,807
Issued: Jul. 3, 2007
Appl. No.: 11/284,836
Filed: Nov. 22, 2005

(30) Foreign Application Priority Data

Dec. 2, 2004 (DE) ..... 10 2004 058 337

(51) Int. Cl.
*C07D 475/00* (2006.01)
*C07D 239/30* (2006.01)

(52) U.S. Cl. ..... 544/257; 544/231

(58) Field of Classification Search ..... 544/257
See application file for complete search history.

(56) References Cited

U.S. PATENT DOCUMENTS

| | | | |
|---|---|---|---|
| 4,957,922 | A | 9/1990 | Lammens et al. |
| 5,043,270 | A | 8/1991 | Abrams et al. |
| 5,167,949 | A | 12/1992 | Ferrand et al. |
| 5,198,547 | A | 3/1993 | Bailey et al. |
| 5,424,311 | A | 6/1995 | Billhardt-Troughton et al. |
| 5,698,556 | A | 12/1997 | Chan |
| 6,096,924 | A | 8/2000 | Studer et al. |
| 6,156,766 | A | 12/2000 | Arita et al. |
| 6,174,895 | B1 | 1/2001 | Kleinman |
| 6,605,255 | B2 | 8/2003 | Kroll et al. |
| 6,806,272 | B2 | 10/2004 | Bauer et al. |
| 6,861,422 | B2 | 3/2005 | Hoffmann et al. |
| 6,875,868 | B2 | 4/2005 | Bonnert et al. |
| 7,238,807 | B2 | 7/2007 | Duran et al. |
| 7,241,889 | B2 | 7/2007 | Hoffmann et al. |
| 7,332,491 | B2 | 2/2008 | Grauert et al. |
| 7,371,753 | B2 | 5/2008 | Stadtmueller et al. |
| 7,414,053 | B2 | 8/2008 | Grauert et al. |
| 7,439,358 | B2 | 10/2008 | Linz et al. |
| 7,547,780 | B2 | 6/2009 | Grauert et al. |
| 7,625,899 | B2 | 12/2009 | Hoffmann et al. |
| 7,626,019 | B2 | 12/2009 | Duran et al. |
| 7,629,460 | B2 | 12/2009 | Grauert et al. |
| 7,700,769 | B2 | 4/2010 | Grauert et al. |
| 7,723,517 | B2 | 5/2010 | Grauert et al. |
| 7,728,134 | B2 | 6/2010 | Linz et al. |
| 7,750,152 | B2 | 7/2010 | Hoffman et al. |
| 7,759,347 | B2 | 7/2010 | Hoffmann |
| 7,759,485 | B2 | 7/2010 | Linz et al. |
| 7,807,831 | B2 | 10/2010 | Grauert et al. |
| 7,816,530 | B2 | 10/2010 | Grauert |
| 2002/0183292 | A1 | 12/2002 | Pairet et al. |
| 2002/0183293 | A1 | 12/2002 | Banerjee et al. |
| 2003/0130286 | A1 | 7/2003 | Denny et al. |
| 2004/0029885 | A1 | 2/2004 | Bauer et al. |
| 2004/0147524 | A1 | 7/2004 | Bauer et al. |
| 2004/0176380 | A1 | 9/2004 | Hoffmann et al. |
| 2005/0014760 | A1 | 1/2005 | Hoffmann et al. |
| 2005/0014761 | A1 | 1/2005 | Hoffmann et al. |
| 2005/0148501 | A1 | 7/2005 | Palmer et al. |
| 2005/0159414 | A1 | 7/2005 | Nickolaus et al. |
| 2005/0165010 | A1 | 7/2005 | Nickolaus et al. |
| 2006/0004014 | A1 | 1/2006 | Hoffmann et al. |
| 2006/0009457 | A1 | 1/2006 | Hoffmann et al. |
| 2006/0025411 | A1 | 2/2006 | Hoffmann et al. |
| 2006/0035902 | A1 | 2/2006 | Linz et al. |
| 2006/0035903 | A1 | 2/2006 | Mohr et al. |
| 2006/0046989 | A1 | 3/2006 | Grauert et al. |
| 2006/0047118 | A1 | 3/2006 | Stadtmueller et al. |
| 2006/0052383 | A1 | 3/2006 | Grauert et al. |
| 2006/0058311 | A1 | 3/2006 | Munzert et al. |
| 2006/0074088 | A1 | 4/2006 | Munzert et al. |

(Continued)

FOREIGN PATENT DOCUMENTS

| | | | |
|---|---|---|---|
| CA | 2458699 | A1 | 3/2003 |

(Continued)

OTHER PUBLICATIONS

Snyder, J. S. et al., "Common bacteria whose susceptibility to antimicrobials is no longer predictable". NCBI, PubMed, 2000, Le Journal Medical Libanais (The Lebanse Medical Journal), 48, pp. 208-214.

Souillac, P. et al., "Characterization of delivery systems, differential scanning calorimetry". (In Encyclopedia of Controlled Drug Delivery), 1999, John Wiley & Sons, pp. 212-227.

Sugar, A. M. et al., "Comparison of three methods of antifungal susceptibility testing with the proposed NCCLS standard broth macrodilution assay: lack of effect of phenol red". Mycology, Diagn Microbiol. Infect. Dis. 1995, 21—pp. 129-133.

Takai, N. et al., "Polo-like kinases (PLKs) and cancer". Oncogene , 2005, 24, pp. 287-291.

Tenbrink, R. E. et al., "Antagonist, partial agonist, and full agonist imidazo[1,5-a]quinoxaline amides and carbamates acting through the BABA/Benzodiazepine receptor". J. Med. Chem. 1994, 37, pp. 758-768.

(Continued)

*Primary Examiner* — Susanna Moore

(74) *Attorney, Agent, or Firm* — Michael P. Morris; Anthony P. Bottino

(57) ABSTRACT

Disclosed are processes for the preparation of fused piperazin-2-one derivatives of general formula (I)

(I)

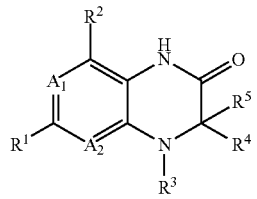

wherein the groups $R^1$ to $R^5$, $A_1$ and $A_2$ have the meanings given in the claims and in the description, particularly the preparation of 7,8-dihydro-5H-pteridin-6-one derivatives and intermediates thereof.

16 Claims, No Drawings

U.S. PATENT DOCUMENTS

| | | | |
|---|---|---|---|
| 2006/0079503 | A1 | 4/2006 | Schwede et al. |
| 2007/0043055 | A1 | 2/2007 | Maier et al. |
| 2007/0208027 | A1 | 9/2007 | Duran et al. |
| 2007/0213528 | A1 | 9/2007 | Duran et al. |
| 2007/0213529 | A1 | 9/2007 | Duran et al. |
| 2007/0213530 | A1 | 9/2007 | Duran et al. |
| 2007/0213531 | A1 | 9/2007 | Duran et al. |
| 2007/0213534 | A1 | 9/2007 | Duran et al. |
| 2007/0219369 | A1 | 9/2007 | Duran et al. |
| 2008/0108812 | A1 | 5/2008 | Grauert et al. |
| 2008/0113992 | A1 | 5/2008 | Grauert et al. |
| 2008/0171747 | A1 | 7/2008 | Hoffman et al. |
| 2008/0177066 | A1 | 7/2008 | Linz et al. |
| 2008/0194818 | A1 | 8/2008 | Grauert et al. |
| 2008/0221099 | A1 | 9/2008 | Munzert et al. |
| 2008/0293944 | A1 | 11/2008 | Hoffmann et al. |
| 2008/0319190 | A1 | 12/2008 | Grauert et al. |
| 2008/0319192 | A1 | 12/2008 | Grauert et al. |
| 2008/0319193 | A1 | 12/2008 | Grauert et al. |
| 2009/0018333 | A1 | 1/2009 | Grauert et al. |
| 2009/0023733 | A1 | 1/2009 | Cage et al. |
| 2009/0029990 | A1 | 1/2009 | Maier et al. |
| 2009/0030004 | A1 | 1/2009 | Linz et al. |
| 2009/0124628 | A1 | 5/2009 | Hoffmann et al. |
| 2009/0143379 | A1 | 6/2009 | Mohr et al. |
| 2009/0238828 | A1 | 9/2009 | Munzert et al. |
| 2009/0280115 | A1 | 11/2009 | Maier et al. |
| 2009/0298840 | A1 | 12/2009 | Linz et al. |
| 2010/0029642 | A1 | 2/2010 | Hoffmann et al. |
| 2010/0249412 | A1 | 9/2010 | Linz et al. |
| 2010/0249458 | A1 | 9/2010 | Linz et al. |
| 2010/0280037 | A1 | 11/2010 | Linz et al. |
| 2010/0324288 | A1 | 12/2010 | Hoffmann et al. |

FOREIGN PATENT DOCUMENTS

| | | | |
|---|---|---|---|
| CA | 2517020 | A1 | 9/2004 |
| CA | 2517010 | A1 | 11/2004 |
| CA | 2576290 | A1 | 2/2006 |
| EP | 143478 | A1 | 6/1985 |
| EP | 347146 | A2 | 12/1989 |
| EP | 399856 | A1 | 11/1990 |
| EP | 429149 | A1 | 5/1991 |
| ES | 2287583 | | 12/2007 |
| RU | 2002125451 | A | 1/2004 |
| WO | 9609045 | A1 | 3/1996 |
| WO | 9634867 | A1 | 11/1996 |
| WO | 9636597 | A1 | 11/1996 |
| WO | WO 96/36597 | | 11/1996 |
| WO | 9811893 | A1 | 3/1998 |
| WO | 0119825 | A1 | 3/2001 |
| WO | 0170741 | A1 | 9/2001 |
| WO | 0178732 | A1 | 10/2001 |
| WO | 02057261 | A2 | 7/2002 |
| WO | 02076954 | A1 | 10/2002 |
| WO | 02076985 | A1 | 10/2002 |
| WO | 03020722 | A1 | 3/2003 |
| WO | WO 03/020722 | A1 | 3/2003 |
| WO | 03093249 | A1 | 11/2003 |
| WO | 04014899 | A1 | 2/2004 |
| WO | 04076454 | A1 | 9/2004 |
| WO | 04093848 | A2 | 11/2004 |
| WO | 05067935 | A1 | 7/2005 |
| WO | 06018182 | A1 | 2/2006 |
| WO | 06018185 | A2 | 2/2006 |
| WO | 06018220 | A2 | 2/2006 |
| WO | 06018221 | A1 | 2/2006 |
| WO | 06021378 | A1 | 3/2006 |
| WO | 07014838 | A1 | 2/2007 |
| WO | 07090844 | A1 | 8/2007 |
| WO | 09019205 | A1 | 2/2009 |

OTHER PUBLICATIONS

Turner, S., "The Design of Organic Syntheses". Elsevier, 1976, pp. 10 and 149.

Turner, W.W.et al., "Recent advances in the medicinal chemistry of antifungal agents". Current Pharmacutical Design, 1996, 2, pp. 209-224.

Verschuren, E.W. et al., "The cell cycle and how it is steered by Kaposi's sarcoma-associated herpesvirus cyclin". Journal of General Virology, 2004, 85, pp. 1347-1361.

Vippagunta, S. R. et al., "Crystalline solids". Advanced Drug Delivery Reviews, 48, 2001, pp. 3-26.

Visiting Nurse Association of America. www.vnaa.org/gen/Germ_Protection_Center_Cold_and_Flu_Resources,html, 2009.

Voskoglou-Nomikos, T. et al., "Clinical predictive value of the in vitro cell line, human xenograft, and mouse allograft preclinical cancer models". Clinical Cancer Research vol. 9, 2003, pp. 4227-4239.

Wagner, B. et al, "7-Benzylamino-6-chloro-2-piperazino-4-pyrrolidino-pteridine, a potent inhibitor of cAMP-specific phosphodiesterase, enhancing nuclear protein binding to the CRE consensus sequence in human tumour cells", Biochemical Pharmacology, Pergamon, Oxford, GB, 2002, pp. 659-668.

Wagner, G. et al., "Synthesis of new phrido[3',2':4,5] thieno '3,2-d] 1,2,3-triazine derivatives as antianaphylactics". Biosciences Dept of the University of Leipzig, Pharmazie (Pharmacy), 48, vol. 7,1993, pp. 514-518.

Webster's Comprehensive Dictionary, 1996, pp. 1013-1014.

Wikipedia. "Melting Point", Jan 17, 2007. http://en.wikipedia.org/wiki/Melting_point.

Wolf, D. E.et al., "The structure of rhizopterin". Contribution from the Research Labs of Merck and Co. Inc. Nov. 1947, Journal of American Chem. Soc., vol. 69, pp. 2753-2759. XP002352205.

ACPS Meeting, Background Information. "Scientific considerations of plymorphism in pharmaceutical solids: abbreviated new drug applications". Oct. 2002.

Ahlenius, T. List of cardiovascular disorder/diseases. Ahlenius, Karolinska Institutet. Stockholm, Sweden. Cardiovascular Diseases, p. 1-34, Apr. 2007.

Ahmad, N. "Polo-like kinase (Plk) 1: a novel target for the treatment of prostate cancer". The FASEB Journal. 2004, 18:5-7. Dept of Dermatology, Univ. Wisconsin, pp. 5-7.

Arnold, K. "Collaboration to play key role in NCI's future, director says". Journal of the National Cancer Institute, Jun. 5, 2002, pp. 790-792, vol. 94, No. 11.

BBC News/Health, Killer Breast Cancern Therapy Hope, www.newsvote.bbc/co./uk, Published Jan. 21, 2006.

Bennett, J.C., et al., "Textbook of Medicine", Part XIV, Oncology, 1997.

Blain, S. W. et al., "Differential interaction of the cyclin-dependent kinase (Cdk) Inhibitor p27KIP with cyclin A-Cdk2 and cyclin D2-Cdk4". The Journal of Biological Chemistry, vol. 272, No. 41, Issue Oct. 10, 1997, pp. 25862-25872.

Chen, J.X. et al., "Parallel differentiated recognition of ketones and acetals". Angewandte Chemie Int. Ed, vol. 37, Issue 1/2, p. 91-93, 1998.

Dipolar aprotic solvent. Exhibit A, IUPAC Compendium of Chemical Terminology, 2nd Edition, 1997.

Doerwald, F.Z. Book Wiley-VCH Verlag GmbH & Co. KGaA, "Side reactions in organice synthesis: A Guide to Successful Synthesis Design". 2005.

Dyson, G, et al. "The Chemistry of Synthetic Drugs". Mir 1964, p. 12-19.

Eurasian Opinion, Appln No. 2007/00389/28, Maly Slatoustinsky per., d.10, kv.15, 101000 Moscow, Russia, "EVROMARKPAT", 2007.

Ferrand, G., et al., "Synthesis and potential antiallergic activity of new pteridinones and related compounds". Eur. J. Med. Chem, 31, 1996, pp. 273-280. XP--2246920.

Ghandi, L., et al., "An Open-Label Phase II Trial of the PLK Inhibitor BI 2536 in Patients with Sensitive Relapse Small Cell Lung Cancer". ASCO Meeting 2009.

Giron, G. "Thernal analysis and calorimetric methods in the characterization of plymorphs and solvates". Thermochimica Acta 248, 1995, pp. 1-59.

Goodman-Gilman's "The Pharmacological Basis of Therapeutics". Ninth edition, 1996, pp. 1225-1271.

International Search Report for PCT/EP2005/056291 mailed Mar. 21, 2006.

Ito, Y., et al., "Polo-like kinase 1 (PLK) expression is associated with cell proliferative activity and cdc2 expression in malignant-lymphoma of the thyroid". Anticancer Research, 2004, vol. 24, No. 1, pp. 259-263.
Jamieson, C. et al., "Application of ReactArray Robotics and Design of Experiments Techniques in Optimisation of Supported Reagent Chemistry". Org. Proc. Res. & Dev., 2002, 6, p. 823-825.
Jaworska, J., et al., "Review of methods for assessing the applicability domains of SARS and QSARS". Sponsor: The European Commission—Joint Research Ctr., Institute for Health and Consumer Protection—ECVAM, Italy, 2004.
Kashima, M. K. et al., "Expression of polo-like kinase (PLK1) in non-Hodgkin's lymphomas". NCBI, PubMed, 2005.
Kimball, S. D. et al., "Cell cycle kinases and checkpoint regulation in cancer". Annual Reports in Medicinal Chemistry, 36, Chapter 14, 2001, pp. 139-148.
Leukemia & Lymphoma Society—Disease Information—Lymphoma. www.leukemia-lymphoma.org/all_page?item_id-7030, 2008.
Leukemia & Lymphoma Society—Disease Information. www.leukemia-lymphoma.org/all_page?item_id-7026, 2008.
Marko, D. et al., "Intracellular localization of 7-benzylamino-6-chloro-2-piperazino-4-pyrrolidino-pteridine in membrane structures impeding the inhibition of cytosolic cyclic AMP-specific phosphodiesterase". Biochemical Pharmacology, 63, 2002, pp. 669-676.
Mashkovkii, M.D., "Medicaments". Moscow, Novaja Volna, 2001, vol. 1, p. 11.
Mashkovskii, M.D. "Drugs", Handbook for Doctors, 1993, Part I, Ch.1, p. 8.
Masuda, Y. et al., "B-Hydroxyisovalerylshikonin induces apoptosis in human leukemia cells by inhibiting the activity of a polo-like kinase 1 (PLK)". 2003, Oncogene, 22, pp. 1012-1023.
Mayer, SF, et al., "Enzyme-initiated domino (cascase) reactions". Chem. Soc. Rev, 2001, p. 332-339.
MedlinePlus: Bacterial Infections. www.nim.nih.gov/medlineplus/print/bacterialinfections.htm, date last updated Mar. 25, 2009.
MedlinePlus: Viral Infections. www.nim.nih.gov/medlineplus/print/viralinfections.htm, date last updated Feb. 11, 2009.
Merck Manual of Medical Information—Home Edition, Section 17. "Parasitic Infections". Chapter 184, 2003.
Mikhailov, I.B., Principles of Rational Pharmacotherapy. Handbook for clinical pharmacology for students of pediatric and medical faculties of medical high schools, St. Petersburg, Russia, "Foliant", 1999, p. 25.
Mito, K., et al., "Expression of polo-like kinase (PLK1) in non-Hodgkin's lymphomas". NCBI, PubMed, 2005, Leuk. Lymphoma, 46(2), pp. 251-231.
Nagao, K. et al., "Effect of MX-68 on airway inflammation and hyperresponsiveness in mice and guinea-pigs". Journal of Pharmacy and Pharmacology, JPP 2004, 56, pp. 187-196.
National Institute of Neurological Disorders, Index Stroke, 2006.
Norman, P. "PDE4 inhibitors". Ashley Publications Ltd., Expert Opinions Ther. Patents, 1999, pp. 1101-1118.
Office Action mailed Dec. 10, 2003 for U.S. Appl. No. 10/226,710, filed Aug. 23, 2002. Inventor: Eckhart Bauer.
Office Action mailed Apr. 28, 2004 for U.S. Appl. No. 10/374,876, filed Feb. 26, 2003. Inventor: Matthias Hoffmann.
Ohio Dept of Health, "Brain and Other Central Nervous System Cancer in Ohio, 1997-2001". Sep. 2004, pp. 1-4.
Organic Chemistry, Grupo Editorial Iberoamerica, Section 13, 3, pp. 301-302, 1983 (best copy available in Spanish).
Rocha Lima, C.M. et al. "Randomized phase II trial of gemcitabine plus irinotecan or docetaxel uin stage IIIB or stage IV NSCLC" Annals of Oncology, 15(3), p. 410-418, 2004.
Rylander, P.N. "Hydrgenation Methods". 1985, Chapter 13.
Rylander, P.N. "Hydrgenation Methods". 1985, Chapters 3, 4.
Rylander, P.N. "Hydrgenation Methods". 1985, Chapters 8, 9, 10, 11.
Rylander, P.N. "Hydrgenation Methods". 1985, Chapter 5, 6, 7.
Rylander, P.N., "Hydrogenation Methods". 1985, Chapters 1, 2.
Santing, R. E. et al., "Brochodilatory and anti-inflammatory properties of inhaled selective phosphodiesterase inhibitors in a guinea pig model of allergic asthma". European Journal of Pharmacology, 429, 2001, pp. 335-344.
Savelli, F. et al., "Heterotricyclic system Part II—synthesis of new pyrido[1'2':4,5]pyrazino[3,2-d] pyrimidines". Bollettino Chimico Farmaceutico, 131(8), Sep. 1992, pp. 309-312.
Science, vol. 310, Oct. 21, 2005, p. 409, Chemistry: One After Another.
Kummer B, et al., "Combination of Radiation and Polo-like Kinase 1 Inhibition with BI6727 in tumour model A431". Vortrag. 20. Symposium •Experimentelle Strahlentherapie und klinische Strahlenbiologie, Exp. Strahlenther. Klin. Strahlenbiol. 20: 93-96 (2011) (Lecture 20, Symposium Experimental Radiation Therapy and Clinical Radiation Biology.).
Kummer, B. et al., Presentation: "Combination of irradiation and polo-like kinase 1 inhibition with BI 6727 in tumour model A 431". OncoRay—National Centre for Radiation Research in Oncology, Dresden 2011, Experimental Radiotherapy and Clinical Radiobiology.
Tenbrink, R. E. et al., "Antagonist, Partial Agonist, and Full Agonist Imi8daxo[1,5-a]quinoxaline Amides and Carbamates Acting through the GABA a/Benzodiazepine Receptor", J. Med. Chem, 1994, 37, 758-768.

PROCESS FOR THE MANUFACTURE OF FUSED PIPERAZIN-2-ONE DERIVATIVES

Matter enclosed in heavy brackets [ ] appears in the original patent but forms no part of this reissue specification; matter printed in italics indicates the additions made by reissue.

APPLICATION DATA

This application claims priority to German application DE 10 2004 058 337.4 filed Dec. 2, 2004.

The invention relates to a process for preparing fused piperazin-2-one derivatives of general formula (I)

(I)

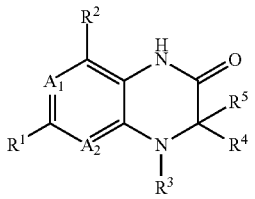

wherein the groups $R^1$ to $R^5$ have the meanings given in the claims and specification, particularly a process for preparing 7,8-dihydro-5H-pteridin-6-one derivatives.

BACKGROUND TO THE INVENTION

Pteridinone derivatives are known from the prior art as active substances with an antiproliferative activity. WO 03/020722 describes the use of dihydropteridinone derivatives for the treatment of tumoral diseases and processes for preparing them.

7,8-Dihydro-5H-pteridin-6-one derivatives of formula (I) are important intermediate products in the synthesis of these active substances. Up till now they have been prepared using methods involving reduction of nitro compounds of formula (II) below, which led to strongly coloured product mixtures and required laborious working up and purification processes.

WO 96/36597 describes the catalytic hydrogenation of nitro compounds using noble metal catalysts with the addition of a vanadium compound, while disclosing as end products free amines, but no lactams.

The aim of the present invention is to provide an improved process for preparing compounds of formula (I), particularly 7,8-dihydro-5H-pteridin-6-one derivatives.

DETAILED DESCRIPTION OF THE INVENTION

The present invention solves the problem outlined above by the method of synthesising compounds of formula (I) described hereinafter.

The invention thus relates to a process for preparing compounds of general formula I (I)

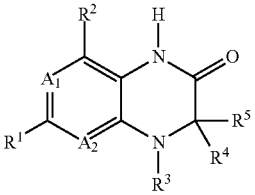

wherein $R^1$ denotes a group selected from the group consisting of chlorine, fluorine, bromine, methanesulphonyl, ethanesulphonyl, trifluoromethanesulphonyl, paratoluenesulphonyl, $CH_3S(=O)$— and phenylS(=O)—

$R^2$ denotes hydrogen or $C_1$-$C_3$-alkyl, $R^3$ denotes hydrogen or a group selected from the group consisting of optionally substituted $C_1$-$C_{12}$-alkyl, $C_2$-$C_{12}$-alkenyl, $C_2$-$C_{12}$-alkynyl and $C_6$-$C_{14}$-aryl, or a group selected from the group consisting of optionally substituted and/or bridged $C_3$-$C_{12}$-Cycloalkyl, $C_3$-$C_{12}$-cycloalkenyl, $C_7$-$C_{12}$-polycycloalkyl, $C_7$-$C_{12}$-polycycloalkenyl, $C_5$-$C_{12}$-spirocycloalkyl and saturated or unsaturated $C_3$-$C_{12}$-heterocycloalkyl, which contains 1 to 2 heteroatoms, $R^4$, $R^5$ which may be identical or different denote hydrogen or optionally substituted $C_1$-$C_6$-alkyl, or $R^4$ and $R^5$ together denote a 2- to 5-membered alkyl bridge which may contain 1 to 2 heteroatoms, or $R^4$ and $R^3$ or $R^5$ and $R^3$ together denote a saturated or unsaturated $C_3$-$C_4$-alkyl bridge, which may optionally contain 1 heteroatom, and $A_1$ and $A_2$ which may be identical or different represent —CH═ or —N═, preferably —N═, in which a compound of formula II (II)

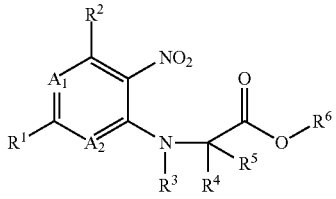

wherein $R^1$-$R^5$ and $A_1$, $A_2$ have the stated meaning and $R^6$ denotes $C_1$-$C_4$-alkyl, a) is hydrogenated with hydrogen in the presence of a hydrogenation catalyst and b) a copper, iron or vanadium compound is added, in which steps a) and b) may take place simultaneously or successively.

In a preferred process, the hydrogenation of the compound of formula II is carried out directly in the presence of the hydrogenation catalyst and the copper, iron or vanadium compound to form the compound of formula I.

In a particularly preferred process, after the first hydrogenation step a), first of all the intermediate product of formula III is obtained, which may optionally be isolated, (III)

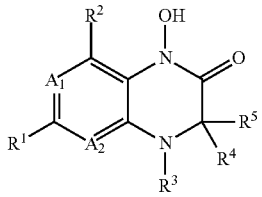

and is then further reduced in the presence of a hydrogenation catalyst and a copper, iron or vanadium compound to form a compound of formula I (I)

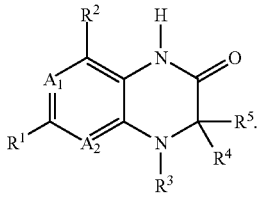

Also preferred is a process in which the hydrogenation catalyst is selected from the group consisting of rhodium, ruthenium, iridium, platinum, palladium and nickel, preferably platinum, palladium and Raney nickel. Platinum is particularly preferred. Platinum may be used in metallic form or oxidised form as platinum oxide on carriers such as e.g. activated charcoal, silicon dioxide, aluminium oxide, calcium carbonate, calcium phosphate, calcium sulphate, barium sulphate, titanium dioxide, magnesium oxide, iron oxide, lead oxide, lead sulphate or lead carbonate and optionally additionally doped with sulphur or lead. The preferred carrier material is activated charcoal, silicon dioxide or aluminium oxide.

Preferred copper compounds are compounds in which copper assumes oxidation states I or II, for example the halides of copper such as e.g. CuCl, $CuCl_2$, CuBr, $CuBr_2$, CuI or $CuSO_4$. Preferred iron compounds are compounds wherein iron assumes oxidation states II or III, for example the halides of iron such as e.g. $FeCl_2$, $FeCl_3$, $FeBr_2$, $FeBr_3$, $FeF_2$ or other iron compounds such as e.g. $FeSO_4$, $FePO_4$ or $Fe(acac)_2$.

Preferred vanadium compounds are compounds wherein vanadium assumes the oxidation states 0, II, III, IV or V, for example inorganic or organic compounds or complexes such as e.g. $V_2O_3$, $V_2O_5$, $V_2O_4$, $Na_4VO_4$, $NaVO_3$, $NH_4VO_3$, $VOCl_2$, $VOCl_3$, $VOSO_4$, $VCl_2$, $VCl_3$, vanadium oxobis(1-phenyl-1,3-butanedionate), vanadium oxotriisopropoxide, vanadium(III)acetylacetonate [$V(acac)_3$] or vanadium(IV) oxyacetylacetonate [$VO(acac)_2$]. Vanadium(IV)oxyacetylacetonate [$VO(acac)_2$] is particularly preferred.

The copper, iron or vanadium compound may be used either directly at the start of the hydrogenation or after the formation of the intermediate of formula (III), as preferred.

Also preferred is a process wherein the amount of added hydrogenation catalyst is between 0.1 and 10 wt.-% based on the compound of formula (II) used.

Also preferred is a process wherein the amount of copper, iron or vanadium compound used is between 0.01 and 10 wt.-% based on the compound of formula (II) used.

Also preferred is a process wherein the reaction is carried out in a solvent selected from the group consisting of dipolar, aprotic solvents, for example dimethylformamide, dimethylacetamide, N-methylpyrrolidinone, dimethylsulphoxide or sulpholane; alcohols, for example methanol, ethanol, 1-propanol, 2-propanol, the various isomeric alcohols of butane and pentane; ethers, for example diethyl ether, methyl-tert.-butylether, tetrahydrofuran, 2-methyltetrahydrofuran, dioxane or dimethoxyethane; esters, for example ethyl acetate, 2-propylacetate or 1-butylacetate; ketones, for example acetone, methylethylketone or methylisobutylketone; carboxylic acids, for example acetic acid; apolar solvents, for example toluene, xylene, cyclohexane or methylcyclohexane, as well as acetonitrile, methylene chloride and water. The solvents may also be used as mixtures.

Also preferred is a process wherein the reaction temperature is between 0° C. and 150° C., preferably between 20° C. and 100° C.

Also preferred is a process wherein the hydrogen pressure is 1 bar to 100 bar.

The invention further relates to a compound of formula (III)

(III)

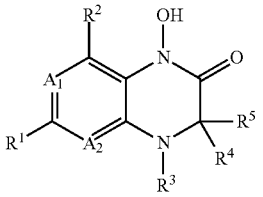

wherein $R^1$ to $R^5$ may have the stated meaning.

Preferred compounds of formula (III) are those wherein $A_1$ and $A_2$ are identical and denote —N═.

The reactions are worked up by conventional methods e.g. by extractive purification steps or precipitation and crystallisation methods.

The compounds according to the invention may be present in the form of the individual optical isomers, mixtures of the individual enantiomers, diastereomers or racemates, in the form of the tautomers as well as in the form of the free bases or the corresponding acid addition salts with acids—such as for example acid addition salts with hydrohalic acids, for example hydrochloric or hydrobromic acid, or organic acids, such as for example oxalic, fumaric, diglycolic or methanesulphonic acid.

Examples of alkyl groups, including those which are part of other groups, are branched and unbranched alkyl groups with 1 to 12 carbon atoms, preferably 1-6, particularly preferably 1-4 carbon atoms, such as for example: methyl, ethyl, propyl, butyl, pentyl, hexyl, heptyl, octyl, nonyl, decyl and dodecyl. Unless otherwise stated, the above-mentioned designations propyl, butyl, pentyl, hexyl, heptyl, octyl, nonyl, decyl and dodecyl include all the possible isomeric forms. For example the term propyl includes the two isomeric groups n-propyl and iso-propyl, the term butyl includes n-butyl, isobutyl, sec. butyl and tert.-butyl, the term pentyl includes isopentyl, neopentyl etc.

In the above-mentioned alkyl groups one or more hydrogen atoms may optionally be replaced by other groups. For example these alkyl groups may be substituted by fluorine. It is also possible for all the hydrogen atoms of the alkyl group to be replaced.

Examples of alkyl bridges, unless otherwise stated, are branched and unbranched alkyl groups with 2 to 5 carbon atoms, for example ethylene, propylene, isopropylene, n-butylene, iso-butyl, sec. butyl and tert.-butyl etc. bridges. Particularly preferred are ethylene, propylene and butylene bridges. In the above-mentioned alkyl bridges 1 to 2 C atoms may optionally be replaced by one or more heteroatoms selected from among oxygen, nitrogen or sulp$^{r.}$ Examples of alkenyl groups (including those which are part of other groups) are branched and unbranched alkylene groups with 2 to 12 carbon atoms, preferably 2-6 carbon atoms, particularly preferably 2-3 carbon atoms, provided that they have at least one double bond. The following are mentioned by way of example: ethenyl, propenyl, butenyl, pentenyl etc. Unless otherwise stated, the above-mentioned designations propenyl, butenyl etc. include all the possible isomeric forms. For example the term butenyl includes 1-butenyl, 2-butenyl, 3-butenyl, 1 -methyl-1-propenyl, 1-methyl-2-propenyl, 2-methyl-1-propenyl, 2-methyl-2-propenyl and 1-ethyl-1-ethenyl.

In the above-mentioned alkenyl groups, unless otherwise described, one or more hydrogen atoms may optionally be replaced by other groups. For example these alkyl groups may be substituted by the halogen atom fluorine. It is also possible for all the hydrogen atoms of the alkenyl group to be replaced.

Examples of alkynyl groups (including those which are part of other groups) are branched and unbranched alkynyl groups with 2 to 12 carbon atoms, provided that they have at least one triple bond, for example ethynyl, propargyl, butynyl, pentynyl, hexynyl etc., preferably ethynyl or propynyl.

In the above-mentioned alkynyl groups, unless otherwise described, one or more hydrogen atoms may optionally be replaced by other groups. For example these alkyl groups may be fluorosubstituted. It is also possible for all the hydrogen atoms of the alkynyl group to be replaced.

The term aryl denotes an aromatic ring system with 6 to 14 carbon atoms, preferably 6 or 10 carbon atoms, preferably phenyl, which, unless otherwise described, may for example carry one or more of the following substituents: OH, $NO_2$, CN, OMe, —$OCHF_2$, —$OCF_3$, halogen, preferably fluorine or chlorine, $C_1$-$C_{10}$-alkyl, preferably $C_1$-$C_5$-alkyl, preferably $C_1$-$C_3$-alkyl, particularly preferably methyl or ethyl, —O—$C_1$-$C_3$-alkyl, preferably —O-methyl or —O-ethyl, —COOH, —COO—$C_1$-$C_4$-alkyl, preferably —O-methyl or —O-ethyl, —$CONH_2$.

Examples of cycloalkyl groups are cycloalkyl groups with 3-12 carbon atoms, for example cyclopropyl, cyclobutyl, cyclopentyl, cyclohexyl, cycloheptyl or cyclooctyl, preferably cyclopropyl, cyclopentyl or cyclohexyl, while each of the above-mentioned cycloalkyl groups may optionally also carry one or more substituents, for example: OH, $NO_2$, CN, OMe, —$OCHF_2$, —$OCF_3$ or halogen, preferably fluorine or chlorine, $C_1$-$C_{10}$-alkyl, preferably $C_1$-$C_5$-alkyl, preferably $C_1$-$C_3$-alkyl, particularly preferably methyl or ethyl, —O—$C_1$-$C_3$-alkyl, preferably —O-methyl or —O-ethyl, —COOH, —COO—$C_1$-$C_4$-alkyl, preferably —COO-methyl or —COO-ethyl or —$CONH_2$. Particularly preferred substituents of the cycloalkyl groups are ═O, OH, methyl or F.

Examples of cycloalkenyl groups are cycloalkyl groups with 3-12 carbon atoms, which have at least one double bond, for example cyclopropenyl, cyclobutenyl, cyclopentenyl, cyclohexenyl or cycloheptenyl, preferably cyclopropenyl, cyclopentenyl or cyclohexenyl, while each of the above-mentioned cycloalkenyl groups may optionally also carry one or more substituents.

"═O" denotes an oxygen atom linked by a double bond.

Examples of heterocycloalkyl groups are, unless otherwise described in the definitions, 3- to 12-membered, preferably 5-, 6- or 7-membered, saturated or unsaturated heterocycles, which may contain nitrogen, oxygen or sulphur as heteroatoms, for example tetrahydrofuran, tetrahydrofuranone, γ-butyrolactone, α-pyran, γ-pyran, dioxolane, tetrahydropyran, dioxane, dihydrothiophene, thiolane, dithiolane, pyrroline, pyrrolidine, pyrazoline, pyrazolidine, imidazoline, imidazolidine, tetrazole, piperidine, pyridazine, pyrimidine, pyrazine, piperazine, triazine, tetrazine, morpholine, thiomorpholine, diazepan, oxazine, tetrahydro-oxazinyl, isothiazole and pyrazolidine, preferably morpholine, pyrrolidine, piperidine or piperazine, while the heterocycle may optionally carry substituents, for example $C_1$-$C_4$-alkyl, preferably methyl, ethyl or propyl.

Examples of polycycloalkyl groups are optionally substituted, bi-, tri-, tetra- or pentacyclic cycloalkyl groups, for example pinane, 2,2,2-octane, 2,2,1-heptane or adamantane.

Examples of polycycloalkenyl groups are optionally bridged and/or substituted, 8- membered bi-, tri-, tetra- or pentacyclic cycloalkenyl groups, preferably bicycloalkenyl or tricycloalkenyl groups, if they contain at least one double bond, for example norbornene.

Examples of spiroalkyl groups are optionally substituted spirocyclic $C_5$-$C_{12}$ alkyl groups.

Halogen generally denotes fluorine, chlorine, bromine or iodine, preferably fluorine, chlorine or bromine, particularly preferably chlorine.

The substituent $R^1$ may represent a group selected from the group consisting of chlorine, fluorine, bromine, methanesulphonyl, ethanesulphonyl, trifluoromethanesulphonyl and para-toluenesulphonyl, preferably chlorine.

The substituent $R^2$ may represent hydrogen or $C_1$-$C_3$-alkyl, preferably hydrogen.

The substituent $R^3$ may represent hydrogen, or a group selected from the group consisting of optionally substituted $C_1$-$C_{12}$-alkyl, $C_2$-$C_{12}$-alkenyl, $C_2$-$C_{12}$-alkynyl, and $C_6$-$C_{14}$-aryl, preferably phenyl, or a group selected from the group consisting of optionally substituted and/or bridged $C_3$-$C_{12}$-Cycloalkyl, preferably cyclopentyl, $C_3$-$C_{12}$-cycloalkenyl, $C_7$-$C_{12}$-polycycloalkyl, $C_7$-$C_{12}$-polycycloalkenyl, $C_5$-$C_{12}$-spirocycloalkyl and saturated or unsaturated $C_3$-$C_{12}$-heterocycloalkyl, which contains 1 to 2 heteroatoms.

The substituents $R^4$, $R^5$ may be identical or different and may represent hydrogen, or optionally substituted $C_1$-$C_6$-alkyl, or $R^4$ and $R^5$ together represent a 2- to 5-membered alkyl bridge which may contain 1 to 2 heteroatoms, or $R^4$ and $R^3$ or $R^5$ and $R^3$ together represent a saturated or unsaturated $C_3$-$C_4$-alkyl bridge, which may optionally contain 1 heteroatom.

$A_1$ and $A_2$ which may be identical or different represent —CH═ or —N═, preferably —N═.

$R^6$ may represent a $C_1$-$C_4$-alkyl, preferably methyl or ethyl.

The compound of formula (II) may be prepared according to methods known from the literature, for example analogously to the syntheses described in WO 03/020722.

The compounds of general formula (I) may be prepared inter alia analogously to the following examples of synthesis. These Examples are, however, intended only as examples of procedures to illustrate the invention, without restricting it to their content. The general synthesis is shown in Scheme (1).

Scheme 1

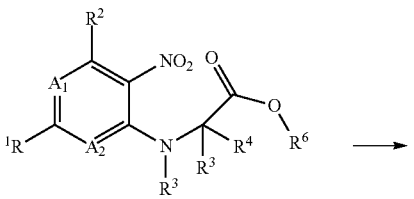

(II)

-continued

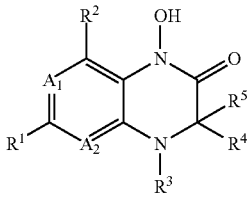

(III)

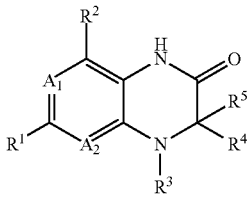

(I)

Synthesis of (7R)-2-chloro-8-cyclopentyl-7-ethyl-5-hydroxy-7,8-dihydro-5H-pteridin-6-one

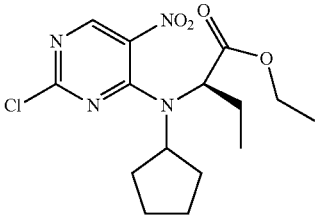

1

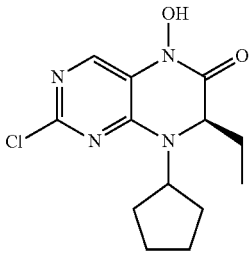

2

30 g (84.2 mmol) of 1 are dissolved in 300 ml tetrahydrofuran and 3 g Pt/C (5%) are added. The reaction mixture is hydrogenated for 5 h at 35° C. and a hydrogen pressure of 4 bar. The catalyst is filtered off and washed with approx. 30 ml of tetrahydrofuran. The filtrate is concentrated by evaporation under reduced pressure. 25.6 g of product 2 are obtained as a yellow solid.

$^1$H-NMR (400 MHZ) (DMSO$_{d6}$): δ 11.05 (bs 1H); 7.85 (s 1H); 4.47-4.45 (dd 1H); 4.16-4.08 (t 1H); 1.95-1.67 (m 10H); 0.80-0.73 (t 3H)

Synthesis of (7R)-2-chloro-8-cyclopentyl-7-ethyl-7,8-dihydro-5H-pteridin-6-one

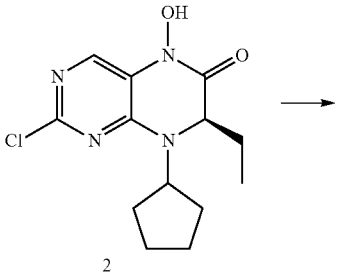

2

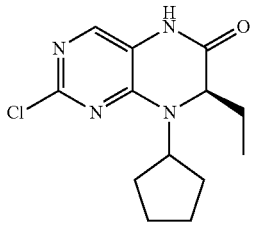

3

5.22 g (17.6 mmol) of 2 are dissolved in 55 ml of tetrahydrofuran. 520 mg Pt-C (5%) and 250 mg vanadium(IV)oxyacetylacetonate are added. The reaction mixture is hydrogenated for 6 hours at 20° C. and a hydrogen pressure of 4 bar. The catalyst is filtered off and washed with approx. 15 ml of tetrahydrofuran. The filtrate is concentrated by evaporation under reduced pressure.

5.0 g of product 3 are obtained as a yellow powder.

$^1$H-NMR (400 MHz) (DMSO$_{d6}$): δ 11.82 (bs 1H); 7.57 (s 1H); 4.24-4.21 (dd 1H); 4.17-4.08 (m 1H); 1.97-1.48 (m 10H); 0.80-0.77 (t 3H).

Synthesis of: (7R)-2-chloro-8-cyclopentyl-7-ethyl-7,8-dihydro-5H-pteridin-6-one 70 g Pt/C (5%)are added to a solution of 700 g (1.96 mol) of 1 in 700 ml of tetrahydrofuran. The reaction mixture is hydrogenated for 2.5 hours at 35° C. and a hydrogen pressure of 4 bar until the hydrogen uptake has stopped. The autoclave is opened and 35 g vanadium(IV)oxyacetylacetonate are added. The mixture is hydrogenated for a further 2.5 hours at 35° C. and a hydrogen pressure of 4 bar. It is filtered and the residue is washed with tetrahydrofuran. The filtrate is concentrated by evaporation under reduced pressure. The residue is dissolved in 2.75 L acetone and precipitated by the addition of an equal amount of demineralised water. The solid is suction filtered and washed with an acetone/water mixture (1:1), then with tert.-butylmethylether. After drying 551 g of product 3 are obtained.

Synthesis of: (7R)-2-chloro-8-cyclopentyl-7-ethyl-7,8-dihydro-5H-pteridin-6-one 30 g (84 mmol) of 1 are dissolved in 300 ml of tetrahydrofuran. 3 g Pt/C (5%) and 1.5 g vanadium(IV)oxyacetylacetonate are added. The reaction mixture is hydrogenated for 24 hours at 35° C. and a hydrogen pressure of 4 bar until the reaction is complete. It is filtered, the residue is washed with tetrahydrofuran and the filtrate is concentrated by evaporation under reduced pressure. The residue is dissolved in 118 ml acetone and precipitated by the addition of an equal amount of demineralised water. The solid is suction filtered and washed with an acetone/water mixture (1:1) and then with tert.-butylmethylether. After drying 18 g of product 3 are obtained.

Synthesis of: (7R)-2-chloro-7-ethyl-8-isopropyl-7,8-dihydro-5H-pteridin-6-one

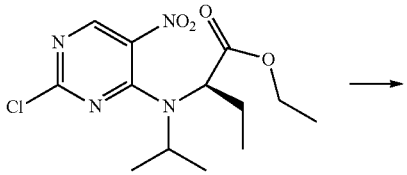

4

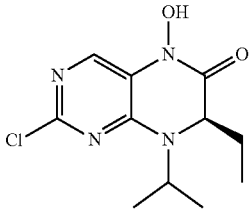

5

10 g (316 mmol) of 4 are dissolved in 800 ml of tetrahydrofuran and 200 ml isopropanol. 10 g Pt/C (5%) and 5 g vanadium(IV)oxyacetylacetonate are added. The reaction mixture is hydrogenated for 24 hours at 35° C. and a hydrogen pressure of 4 bar until the reaction is complete. It is filtered and the filtrate is evaporated down until crystallisation sets in. 150 ml isopropanol are added and the suspension is heated to 70-80° C. until fully dissolved. After the addition of 600 ml demineralised water the product is brought to crystallisation. It is suction filtered and washed with demineralised water. After drying 68 g of product 5 are obtained.

$^1$H NMR (400 MHz) (DMSO$_{d6}$): δ 10.81 (bs 1H); 7.56 (s 1H); 4.37-4.24 (m 2H); 1.89-1.65 (m 2H); 1.34-1.31 (m 6H); 0.80-0.73 (t 3H)

What is claimed is:

1. A Process for preparing compounds of the formula I (I)

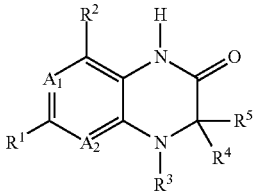

wherein $R^1$ denotes a group selected from the group consisting of chlorine, fluorine, bromine, methanesulphonyl, ethanesulphonyl, trifluoromethanesulphonyl, para-toluenesulphonyl, $CH_3S(=O)$— and phenylS(=O)—, $R^2$ denotes hydrogen or $C_1$-$C_3$-alkyl, $R^3$ denotes hydrogen or a group selected from the group consisting of optionally substituted $C_1$-$C_{12}$-alkyl, $C_2$-$C_{12}$-alkenyl, $C_2$-$C_{12}$-alkynyl and $C_6$-$C_{14}$-aryl, or a group selected from the group consisting of optionally substituted and/or bridged $C_3$-$C_{12}$-cycloalkyl, $C_3$-$C_{12}$-cycloalkenyl, $C_7$-$C_{12}$-polycycloalkyl, $C_7$-$C_{12}$-polycycloalkenyl, $C_5$-$C_{12}$-spirocycloalkyl and saturated or unsaturated $C_3$-$C_{12}$-heterocycloalkyl, which contains 1 to 2 heteroatoms, $R^4$, $R^5$ which may be identical or different denote hydrogen or optionally substituted $C_1$-$C_6$-alkyl, or $R^4$ and $R^5$ together denote a 2- to 5-membered alkyl bridge, which may contain 1 to 2 heteroatoms, or $R^4$ and $R^3$ or $R^5$ and $R^3$ together denote a saturated or unsaturated $C_3$-$C_4$-alkyl bridge, which may optionally contain 1 heteroatom, and "A1 and A2 denote —N═", comprising a) hydrogenating with hydrogen in the presence of a hydrogenation catalyst and a compound of formula II (II)

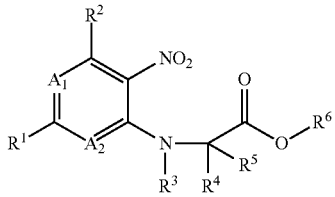

wherein $R^1$ to $R^5$, $A_1$ and $A_2$ have the meanings given above and $R^6$ denotes $C_1$-$C_4$-alkyl, and b) adding a copper, iron or vanadium compound, wherein in which steps a) and b) may take place simultaneously or successively *wherein* step b) [followed by] *follows* step a).

2. The Process according to claim 1, wherein in step b) a copper compound is added.

3. The Process according to claim 1, wherein in step b) an iron compound is added.

4. The Process according to claim 1, wherein in step b) a vanadium compound is added.

5. The Process according to claim 1 wherein steps a) and b) are carried out successively *wherein step b) follows step a*).

6. The Process according to claim 5, wherein that after the first step a) the intermediate product of formula III is first obtained, which may optionally be isolated, (III)

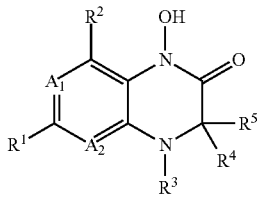

and after the subsequent step b) a compound of formula I is obtained.

7. The Process according to claim 1, wherein steps a) and b) are carried out simultaneously.

8. The Process according to claim 1, wherein the hydrogenation catalyst is selected from the group consisting of rhodium, ruthenium, iridium, platinum, palladium and nickel.

9. The Process according to claim 1, wherein the amount of hydrogenation catalyst added is between 0.1 and 10 wt.-%, based on the compound of formula (II) used.

10. The Process according to claim 1, wherein the amount of copper, iron or vanadium compound added is between 0.01 and 10 wt-%, based on the compound of formula (II) used.

11. The Process according to claim 1, wherein the reaction is carried out in a solvent or mixture of solvents selected from the group consisting of [dipolar, aprotic solvents,] alcohols, ethers, esters, carboxylic acids, [apolar solvents,] acetonitrile, methylene chloride and water.

12. The Process according to claim 1, wherein the reaction temperature is between 0° C. and 150° C.

13. The Process according to claim 1, wherein the hydrogen pressure is from 1 bar to 100 bar.

14. A Process for preparing compounds of the formula I (I)

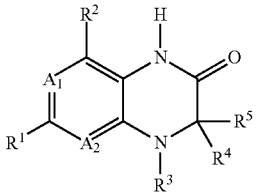

wherein $R^1$ denotes a group selected from the group consisting of chlorine, fluorine, bromine, methanesulphonyl, ethanesulphonyl, trifluoromethanesulphonyl, para-toluenesulphonyl, $CH_3S(=O)$— and phenylS(=O)—, $R^2$ denotes hydrogen or $C_1$-$C_3$-alkyl, $R^3$ denotes hydrogen or a group selected from the group consisting of optionally substituted [C1-C12-alkyl, C2-C12-alkenyl, C2-C12-alkynyl] *$C_1$-$C_{12}$-alkyl, $C_2$-$C_{12}$-alkenyl, $C_2$-$C_{12}$-alkynyl* and $C_6$-$C_{14}$-aryl, or a group selected from the group consisting of optionally substituted and/or bridged $C_3$-$C_{12}$-cycloalkyl, $C_3$-$C_{12}$-cycloalkenyl, $C_7$-$C_{12}$-polycycloalkyl, $C_7$-$C_{12}$-polycycloalkenyl, $C_5$-$C_{12}$-spirocycloalkyl and saturated or unsaturated $C_3$-$C_{12}$-heterocycloalkyl, which contains 1 to 2 heteroatoms, $R^4$, $R^5$ which may be identical or different denote hydrogen or optionally substituted $C_1$-$C_6$-alkyl, or $R^4$, $R^5$ together denote a 2- to 5-membered alkyl bridge, which may contain 1 to 2 heteroatoms, or $R^4$ and $R^3$ or $R^5$ and $R^3$ together denote a saturated or unsaturated $C_3$-$C_4$-alkyl bridge, which may optionally contain 1 heteroatom, and $A_1$ and $A_2$ denote —N═, comprising hydrogenating a compound of formula III with hydrogen in the presence of a hydrogenation catalyst and a copper, iron or vanadium compound (III)

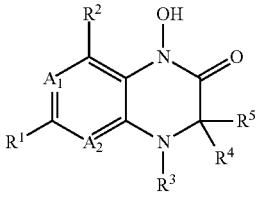

wherein $R^1$ to $R^5$ and $A_1$, $A_2$ have the meanings given above in this claim.

*15. The Process according to claim 11, wherein the solvent or mixture of solvents is:*

*alcohols selected from ethanol, 1-propanol and 2-propanol,*

*ethers selected from diethyl ether, methyl-tert.-butylether, tetrahydrofuran, 2-methyltetrahydrofuran, dioxane and dimethoxyethane,*

*esters selected from ethyl acetate, 2-propylacetate or 1-butylacetate,*

*acetic acid, acetonitrile, methylene chloride or water.*

*16. The Process according to claim 15, wherein the solvent is 2-propanol or tetrahydrofuran or mixtures thereof.*

* * * * *